(12) United States Patent
Liu et al.

(10) Patent No.: US 11,896,580 B2
(45) Date of Patent: Feb. 13, 2024

(54) COMPOSITION FOR IMPROVING MILK QUALITY AND PREPARATION METHOD AND APPLICATION THEREOF

(71) Applicant: CHINA AGRICULTURAL UNIVERSITY, Beijing (CN)

(72) Inventors: Guoshi Liu, Beijing (CN); Hao Wu, Beijing (CN); Yongqiang Lu, Beijing (CN); Lu Zhang, Beijing (CN); Hui Ma, Beijing (CN); Yi Chang, Beijing (CN); Qiaoxiang Liu, Beijing (CN); Songyang Yao, Beijing (CN); Pengyun Ji, Beijing (CN)

(73) Assignee: CHINA AGRICULTURAL UNIVERSITY, Beijing (CN)

( * ) Notice: Subject to any disclaimer, the term of this patent is extended or adjusted under 35 U.S.C. 154(b) by 0 days.

(21) Appl. No.: 17/502,735

(22) Filed: Oct. 15, 2021

(65) Prior Publication Data

US 2022/0117939 A1    Apr. 21, 2022

(30) Foreign Application Priority Data

Oct. 16, 2020   (CN) .......................... 202011111148.4

(51) Int. Cl.
*A61K 31/4045* (2006.01)
*A61P 15/14* (2006.01)

(52) U.S. Cl.
CPC .......... *A61K 31/4045* (2013.01); *A61P 15/14* (2018.01)

(58) Field of Classification Search
CPC ............................ A61K 31/4045; A61P 15/14
See application file for complete search history.

(56) References Cited

U.S. PATENT DOCUMENTS 5,519,047 A * 5/1996 Shelby ............... A61K 31/4045
514/885
6,403,631 B1 6/2002 Sharp et al.
(Continued)

FOREIGN PATENT DOCUMENTS

CN      104688380 A    6/2015
CN      104784171 A    7/2015
(Continued)

OTHER PUBLICATIONS

First Office Action and English Translation issued in corresponding Chinese Application No. 202011111148.4 dated Jun. 24, 2021, 14 pages.
(Continued)

*Primary Examiner* — San Ming R Hui
(74) *Attorney, Agent, or Firm* — Nixon & Vanderhye P.C.

(57) ABSTRACT

The disclosure discloses a composition containing melatonin as an effective ingredient, and its application in improving DHI production performance and improving milk quality. The composition containing melatonin as an effective ingredient according to the present disclosure can significantly reduce the somatic cell count in milk and improve milk quality. Under the conditions of different seasons, ages, and lactation periods, the administration of the composition containing melatonin as an active ingredient according to the present disclosure can significantly reduce the somatic cell score of cow milk (p<0.01), increase the protein content and lactose content in milk, and meanwhile reduce the fat content and urea nitrogen content in milk. In summary, the composition containing melatonin as an effective ingredient according to the present disclosure can improve the quality of milk and increase the efficiency of dairy cow breeding.

4 Claims, 13 Drawing Sheets

A

The effect of melatonin on SCS in different seasons

B

The effect of melatonin on the daily production milk in different seasons

(56) References Cited

U.S. PATENT DOCUMENTS

| | | |
|---|---|---|
| 2017/0348281 A1 | 12/2017 | Liu |
| 2021/0106559 A1 | 4/2021 | Liu |
| 2022/0117940 A1 | 4/2022 | Liu et al. |

FOREIGN PATENT DOCUMENTS

| | | |
|---|---|---|
| CN | 105613423 A | 6/2016 |
| CN | 110447778 A | 11/2019 |
| CN | 110495967 A | 11/2019 |
| CN | 110946859 A | 4/2020 |

OTHER PUBLICATIONS

Minghui Yang et al., "Exogenous melatonin reduces somatic cell count of milk in Holstein cows", Scientific Reports, 7:43280, DOI:10.1038/srep43280, pp. 1-7, 2017.

Second Office Action and English Translation issued in corresponding Chinese Application No. 202011111148.4 dated Jan. 5, 2022, 13 pages.

Auldist, M. J., et al., "Effects of melatonin on the yield and composition of milk from grazing dairy cows in New Zealand," Journal of Dairy Research, 74:52-57 (2007).

Boulanger, V., et al., "Protective Effect of Melatonin and Catalase in Bovine Neutrophil-induced Model of Mammary Cell Damage," J. Dairy Sci., 85:562-569 (2002).

Dairy Herd Management, "Move injections to the neck," Jun. 8, 2012, 2 pages.

Gao, X., "Effects of melatonin on synchronous ovulation and timed insemination artificial in heifers," Database of Excellent Master's Dissertations in China, Agricultural Science and Technology Series, 3:1-31 (2020), with English abstract.

Gitto, E., et al., "Individual and synergistic antioxidative actions of melatonin: studies with vitamin E, vitamin C, glutathione and desferrrioxamine (desferoxamine) in rat liver homogenates," Journal of Pharmacy and Pharmacology, 53:1393-1401 (2001).

Jiménez, A., et al., "Effect of melatonin implants on somatic cell counts in dairy goats," Small Ruminant Research, 84:116-120 (2009).

Li, Z., et al., "Effect of nutritional factors on SCC in dairy cattle," China Feed, 14:29-31, 40 (2014), English abstract.

Liu, S., et al., "Effect of Dietary Biologic Antioxidant Supplementation on Somatic Cell Count of Raw Milk," Dairy Science and Technology, 4:179-182 (2010), English abstract.

Matsui, T., "Vitamin C in Cattle," Asian-Aust. J. Anim. Sci., 25(5):597-605 (2012).

Neto, A. C. R., et al., "Solubility of Vitamin C in Water, Ethanol, Propan-1-ol, Water + Ethanol, and Water + Propan-1-ol at (298.15 and 308.15) K," J. Chem. Eng. Data, 55: 1718-1721 (2010).

Ovid, D., et al., "Melatonin Administration Methods for Research in Mammals and Birds," Journal of Biological Rhythms, 33(6):567-588 (2018).

Sharma, N., et al., "Relationship of Somatic Cell Count and Mastitis: An Overview," Asian-Aust. J. Anim. Sci., 24(3): 429-438 (2011).

First Office Action and English Translation issued for corresponding Chinese Application No. 202011112550.4, dated Jun. 21, 2021, 14 pages.

U.S. Appl. No. 15/540,002, filed Jun. 26, 2017, LIU, related application.

U.S. Appl. No. 17/502,761, filed Oct. 15, 2021, LIU et al., related application.

U.S. Appl. No. 17/078,531, filed Oct. 23, 2020, LIU, related application.

* cited by examiner

Figure 1

The effect of melatonin on SCS in different seasons

The effect of melatonin on the daily production milk in different seasons

The effect of melatonin on the milk protein ratio in dfferent seasons

D

The effect of melatonin on the ratio of lactose to milk in different seasons

The effect of melatonin on the proportion of milk fat in dfferent seasons

F

The effect of melatonin on the content of milk dry matter ratio in dfferent seasons

The effect of melatonin on the nitrogen content of milk in dfferent seasons

Figure 2

The effect of melation on SCS in different ages

The effect of melation on the daily prodution of milk in different ages

Figure 2 (continued)

The effect of melation on the milk protein ratio in different ages

The effect of melatonin on the ratio of lactose to milk in different ages

The effect of melation on the proportion of milk fat in different ages

F

The effect of melatonin on the content of milk dry matter in different ages

The effect of melatonin on the nitrogen content of milk in different ages

The effect of melatonin on SCS in dfferent lactation stages

B

The effect of melatonin on the daily production milk in dfferent lactation stages

The effect of melatonin on the milk protein ratio in dfferent lactation stages

D

The effect of melatonin on the ratio of lactose to milk in different lactation stages

The effect of melatonin on the proportion of milk fat in dfferent lactation stages

F

The effect of melatonin on the content of milk dry matter ratio in dfferent seasons

The effect of melatonin on the nitrogen content of milk in dfferent lactation stages

Figure 4

COMPOSITION FOR IMPROVING MILK QUALITY AND PREPARATION METHOD AND APPLICATION THEREOF

This application claims priority to Chinese Patent Application No. 202011111148.4 filed Oct. 16, 2020, the entire contents of which are hereby incorporated by reference.

TECHNICAL FIELD

The disclosure relates to the field of animal husbandry and veterinary medicine, in particular, to a composition for improving milk quality, as well as a preparation method and application thereof.

BACKGROUND

With the rapid economic and social development, people's demand for dairy products has gradually increased, and the dairy farming industry has shown a trend of rapid development. However, the industrial development is restricted by high breeding costs and poor management experience, due to the late start of the dairy farming industry in China. Dairy Herd Improvement (DHI), as an important means of pasture management, is applied to improve the performance of dairy herd and increase breeding benefits. In the DHI data, the somatic cell count, lactose, milk fat and milk protein are all important indicators that can determine the milk quality. The DHI indicators are affected by many factors. Individual dairy cows may have different DHI indicators due to different seasons, different ages and different lactation periods. If the somatic cell count of milk is too high, the quality of fresh milk will be reduced. Lactose can provide energy to the body and be a unique ingredient in breast milk, many infant formula and dairy products. Milk fat is a complex mixture composed of various types of fats, and is the main component for providing energy. The milk protein mainly comprises casein, and a small amount of albumin and globulin. The milk protein is an important source of nutritional and high-quality proteins in human diet. Urea nitrogen can reflect the efficiency of nitrogen metabolism and the effectivity of protein metabolism in the rumen. It can provide a basis for more accurately regulating full-price rations by determining urea nitrogen content. Changes in DHI indicators will affect the quality of fresh milk and processed products. The more balanced the proportion of the ingredients in fresh milk, the higher its nutritional value.

Melatonin (MT) is mainly secreted by the pineal gland and is an important neuroendocrine active substance in the body. Melatonin can improve the immunity of organism by regulating the secretion of some substances such as immune factors, proteolytic enzymes and prostaglandin. Recent studies have shown that melatonin plays an important role in regulating the differentiation and synthesis of adipose (Acuna-Castroviejo, D., et al.). Melatonin can also regulate immunity, promote the proliferation of T and B lymphocytes, stimulate the production of cytokines, and participate in the regulation of nerve-endocrine-immune network. Humoral and cellular immunity can be enhanced by feeding melatonin. It has showed that immunity can be significantly enhanced by feeding melatonin alone.

In recent years, the research and application of melatonin in the dairy industry have been reported. However, there are still certain limitations, and there are many problems that have not been resolved.

Therefore, it is necessary to find an effective and feasible way to improve the DHI production performance and improve the quality of milk.

SUMMARY

In order to solve the problems existing in the prior art, the present disclosure aims to provide a composition for improving the milk quality of a dairy cow, which has a somatic cell count of 300,000/mL to 1,000,000/mL, as well as the preparation method and application thereof.

The present disclosure provides the following technical solutions in order to achieve the objects of the present disclosure.

According to the first aspect of the present disclosure, provided is a composition for improving milk quality, which comprises an active ingredient containing melatonin.

Preferably, the active ingredient of the composition may be melatonin.

Further, the composition may comprise melatonin at a concentration of 1 to 20 mg/mL; preferably at a concentration of 2.32 to 18.56 mg/mL; more preferably, at a concentration of 4.64 to 9.28 mg/mL; further more preferably, at a concentration of 4.64 mg/mL.

Further, the composition may also comprise absolute ethanol and physiological saline, in which the volume ratio of absolute ethanol to physiological saline is preferably in a range of (1-3):(1-2), more preferably 3:2.

Preferably, physiological saline may be 0.9% physiological saline.

Furthermore, the composition of the present disclosure may be in the form of an injection.

According to the second aspect of the present disclosure, provided is a method for the preparing the above composition, which comprises the following steps: dissolving melatonin in absolute ethanol and then adding physiological saline, wherein the steps are carried out in dark.

According to the third aspect of the present disclosure, provided is a method for improving milk quality by using the above composition or using a composition prepared by the above method, the method for improving milk quality comprises administering the composition of the present disclosure or the composition prepared by the method of the present disclosure to a dairy cow having a somatic cell count of 300,000/mL to 1,000,000/mL.

According to a preferred embodiment, the improvement of the milk quality comprises one or more selected from a group consisting of:

(1) reducing a somatic cell count in milk;
(2) increasing a milk protein content;
(3) increasing a lactose content;
(4) increasing a dry matter content in milk;
(5) reducing a fat content; and
(6) reducing a urea nitrogen content.

According to a preferred embodiment, the composition may be administered by injection.

According to a preferred embodiment, the dose of injection may be in a range of 2 to 3 mL, preferably be 2 mL.

According to a preferred embodiment, the composition may be administered by injection once a day for 3 to 6 consecutive days, preferably for 4 consecutive days.

If the composition is administered by injection for a shorter period, for example, less than 2 consecutive days, there is no obvious improvement in DHI indicators. If the composition is administered by injection for a longer period, for example, more than 7 consecutive days, there is no obvious increase in the improvement of DHI indicators.

Therefore, the composition of the present disclosure is preferably administered to a cow by injection for 3 to 6 consecutive days, considering cost-effectiveness.

According to a preferred embodiment, the present disclosure provides a method for improving milk quality, which comprises subcutaneously injecting, for 4 consecutive days, the composition containing melatonin as an active ingredient according to the present disclosure to a dairy cow having a somatic cell count of 300,000/mL to 1,000,000/mL.

Further, the concentration of melatonin may be in a range of 1 to 20 mg/mL, preferably in a range of 2.32 to 18.56 mg/mL, more preferably in a range of 4.64 to 9.28 mg/mL, further more preferably be 4.64 mg/mL.

Further, melatonin may be administered at a dose of 2 to 3 mL.

Preferably, melatonin may be administered at a dose of 2 mL.

According to the fourth aspect of the present disclosure, provided is use of the composition according to the present disclosure or the composition prepared by the above method for improving the milk quality of a dairy cow having a somatic cell count of 300,000/mL to 1,000,000/mL.

According to a preferred embodiment, the improvement of the milk quality comprises one or more selected from a group consisting of:
(1) reducing a somatic cell count in milk;
(2) increasing a milk protein content;
(3) increasing a lactose content;
(4) increasing a dry matter content in milk;
(5) reducing a fat content; and
(6) reducing a urea nitrogen content.

Preferably, in said use, the composition according to the present disclosure may be administered to a dairy cow by subcutaneous injection.

Further, the concentration of the melatonin may be in a range of 1 to 20 mg/mL, preferably in a range of 2.32 to 18.56 mg/mL, more preferably in a range of 4.64 to 9.28 mg/mL, further more preferably be 4.64 mg/mL.

Further, melatonin may be administered at a dose of 2 to 3 mL.

Preferably, melatonin may be administered at a dose of 2 mL.

The technical solutions provided by the present disclosure at least comprise the following beneficial effect.

The present disclosure provides a composition for improving milk quality, as well as the preparation method and application thereof. Melatonin can be dissolved in absolute ethanol and then added to physiological saline, to give an injection. Such injection can be administered to Holstein cows having a somatic cell count of 300,000/mL to 1,000,000/mL, to reduce the somatic cell count in milk and improve the milk quality. It can provide useful reference for further research to improve the milk quality of dairy cows.

It is found in the present disclosure through animal experimentation that injecting the composition containing melatonin as an active ingredient of the present disclosure in different seasons, ages or lactation periods has a certain regularity in the impact on DHI indicators. Under different seasons, ages or lactation periods, the injection of the melatonin-containing composition of the present disclosure can significantly reduce the somatic cell score (SCS) ($p<0.01$), fat content in milk, and increase the protein and lactose contents in milk. Comprehensive analysis has showed that, for the DHI indicators, melatonin caused the greatest reduction, 63.54%, in SCS, followed by the fat and urea nitrogen contents, the reductions of which were 11.31% and 11.08% respectively. The subcutaneous injection of melatonin can significantly reduce the somatic cell count in milk, improve the milk quality, and increase the efficiency of dairy farming. Therefore, the research and development of melatonin in dairy farming is of great significance.

DETAILED DESCRIPTION OF THE INVENTION

The following examples are merely used to illustrate the present invention, but are not intended to limit the scope of the present invention.

The reagents and materials used in the following examples are all commercially available products.

The purity of Melatonin is required to reach 99.9%.

Example 1. Preparation Process for the Injections of Melatonin

Materials: melatonin and absolute ethanol.
Preparation process: accurately weigh 464.54 mg of melatonin, dissolve it with absolute ethanol in a 100 mL volumetric flask and stir well, then add 0.9% of physiological saline and stir well, set a final volume of 100 mL (anhydrous ethanol:saline=3:2), and finally dispense into 2 mL injection dose. The whole process is done in a dark room.

Example 2. Analysis of the DHI Indicators of Milk after Subcutaneous Injection of Melatonin 1. Experimental Process
(1) According to the monthly DHI test reports from the dairy farm, Holstein cows having somatic cell counts of 300,000/mL to 1,000,000/mL are selected to be fed separately, and are ensured to have no significant difference in physical health. Season groups: spring n=90, summer n=74, autumn n=83, winter n=81 (number of cows). Age groups: 2-year-old n=23; 3-year-old n=80; 4-year-old n=66; 5-year-old n=56; 6-year-old n=27; 7-year-old n=19 (number of cows). Lactation period groups: peak-lactation n=15, mid-lactation n=38, end-lactation n=59 (number of cows) (initial-lactation: days 1-15 after calving; peak-lactation: days 16-100 after calving; mid-lactation: days 101-200 after calving; end-lactation: day 201 after calving to weaning).

(2) The dairy cows having high somatic cell counts are injected with 2 mL melatonin solution every day for 4 consecutive days in each month. 15 days after the injection, fresh milk was collected and stored in 50 mL centrifuge tubes, and was tested for the changes in somatic cell counts. The cows were fed with total mixed ration, and were fed three times at 06:00, 12:00, and 18:00 respectively. Then, the cows entered the sports ground to move freely, drink water and rest.

(3) The sampling bottles were numbered and added with 2-3 drops of potassium dichromate saturated solution, and were used for collecting the milk samples from the milk by the first milking of the cows. The milk sample for each cow was in a volume of 40 mL and placed in a centrifuge tube. After sampling, all the remaining milk was drained from the tubes which were cleaned to avoid contamination between the samples. The samples were stored at 2-7° C. The instrument for measuring the DHI indicators is Milkscan FT+&FC automatic milk compositional analyzer and somatic cell counter. The measurement was carried out in the National Laboratory for Preparation of Standard Materials of DHI.

2. Experimental Results (1) The somatic cell scores of the milk were significantly reduced in all seasons, with the greatest reduction in summer (FIG. 1A). The protein content was significantly increased ($p<0.05$) by injecting melatonin in autumn (3.51%±0.05 VS 3.64%±0.05) (FIG. 1C). The lactose content was increased after injecting melatonin, and was increased significantly in spring (4.89%±0.02 VS 4.94%±0.02), summer (4.96%±0.03 VS 5.06%±0.02) and autumn (4.99%±0.03 VS 5.07%±0.04) ($p<0.05$) (FIG. 1D). The fat content was decreased after injecting melatonin, and was decreased significantly in spring (5.18%±0.12 VS 4.78%±0.14) ($p<0.05$) (FIG. 1E).

Figure 1:
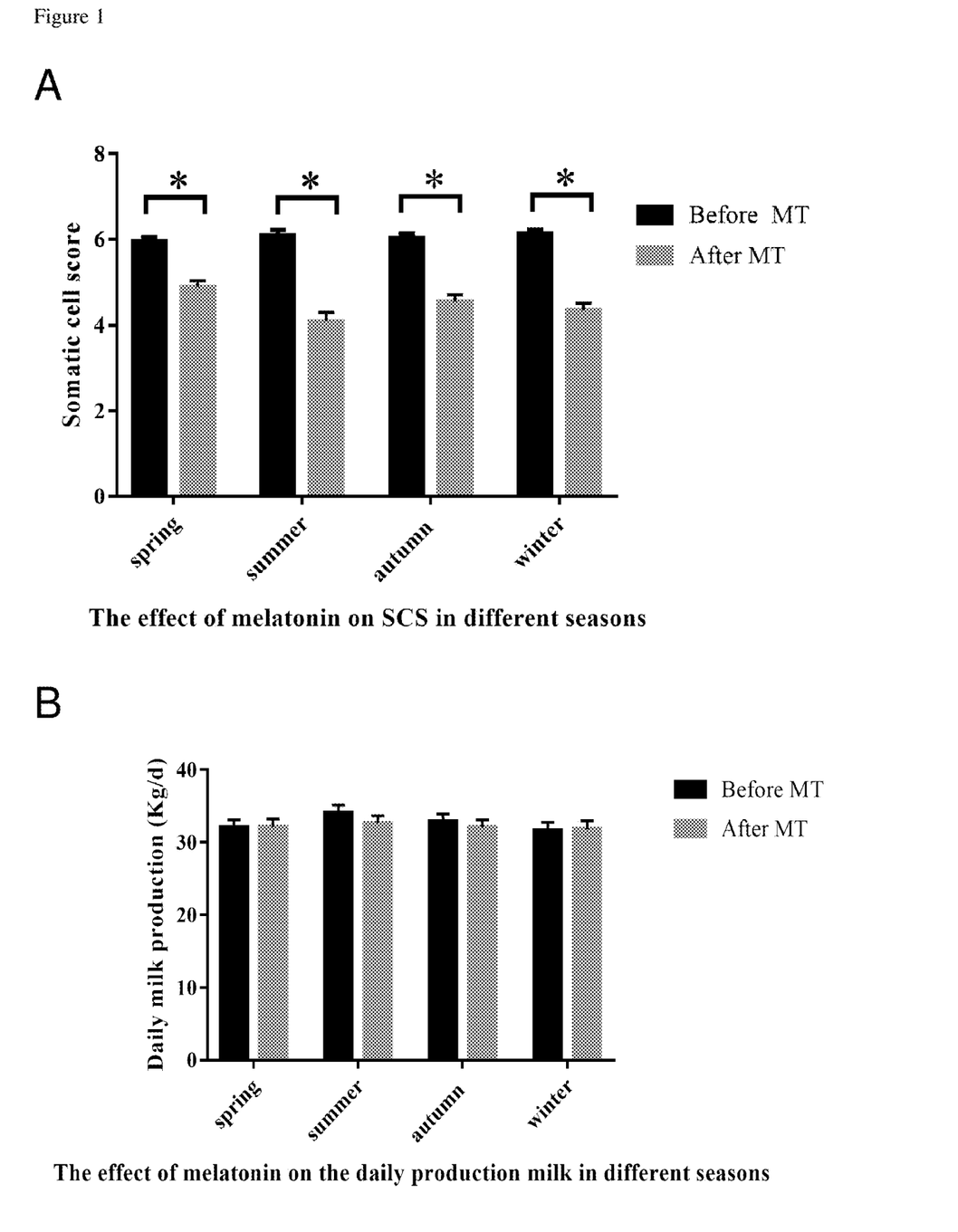
FIG. 1 is a diagram showing the effect of the injection of melatonin on DHI indicators of the milk from dairy cows in different seasons.

The results are shown in FIG. 1, in which:
A. changes in somatic cell scores:
   spring (5.96±0.08 VS 4.89±0.15),
   summer (6.06±0.12 VS 4.09±0.20),
   autumn (6.03±0.11 VS 4.55±0.16), and
   winter (6.12±0.11 VS 4.34±0.17);
B. changes in milk production:
   spring (32.08±1.04 VS 32.11±1.15, kg/d),
   summer (34.09±1.06 VS 32.69±1.00, kg/d),
   autumn (32.88±1.02 VS 32.07±1.05, kg/d), and
   winter (31.67±1.11 VS 31.82±1.17, kg/d);
C. changes in protein contents:
   spring (3.46%±0.04 VS 3.49%±0.04),
   summer (3.45%±0.06 VS 3.45%±0.04),
   autumn (3.51%±0.05 VS 3.64%±0.05), and
   winter (3.39%±0.05 VS 3.43%±0.05);
D. changes in lactose contents:
   spring (4.89%±0.02 VS 4.94%±0.02),
   summer (4.96%±0.03 VS 5.06%±0.02),
   autumn (4.99%±0.03 VS 5.07%±0.04), and
   winter (4.70%±0.07 VS 4.84%±0.04);
E. changes in fat contents:
   spring (5.18%±0.12 VS 4.78%±0.14),
   summer (4.48%±0.16 VS 4.20%±0.12),
   autumn (4.80%±0.11 VS 4.68%±0.13), and
   winter (4.82%±0.10 VS 4.75%±0.11);
F. changes in dry matter contents:
   spring (14.23%±0.14 VS 13.92%±0.15),
   summer (13.61%±0.17 VS 13.42%±0.13),
   autumn (14.00%±0.13 VS 14.10%±0.14), and
   winter (13.68%±0.10 VS 13.65%±0.12);
G. changes in urea nitrogen contents:
   spring (13.08±0.39 VS 14.35±0.45, mg/dL),
   summer (16.59±0.64 VS 14.19±0.50, mg/dL),
   autumn (12.14±0.43 VS 11.72±0.36, mg/dL), and
   winter (17.39±0.47 VS 15.94±0.51, mg/dL);
wherein, spring n=90, summer n=74, autumn n=83, and winter n=81 (unit: number of cows).

(2) Injection of melatonin reduced the somatic cell scores of the milk from Holstein cows at different ages, and had significant effect in Holstein cows of 2-, 3-, 4-, 5- and 7-year-old ($p<0.05$) (FIG. 2A). The lactose content was increased by injecting melatonin, and was significantly increased in cows of 3- (4.95%±0.03 VS 5.03%±0.02) and 4-year-old (4.80%±0.04 VS 4.94%±0.03) ($p<0.05$) (FIG. 2D). The fat content was reduced by injecting melatonin, and was significantly reduced in cows of 3-year-old ($p<0.05$) (FIG. 2E). The dry matter content of the milk was significantly reduced by injecting melatonin in Holstein cows of 3-year-old (13.82%±0.12 VS 13.57%±0.13) (FIG. 2F).

Figure 2:
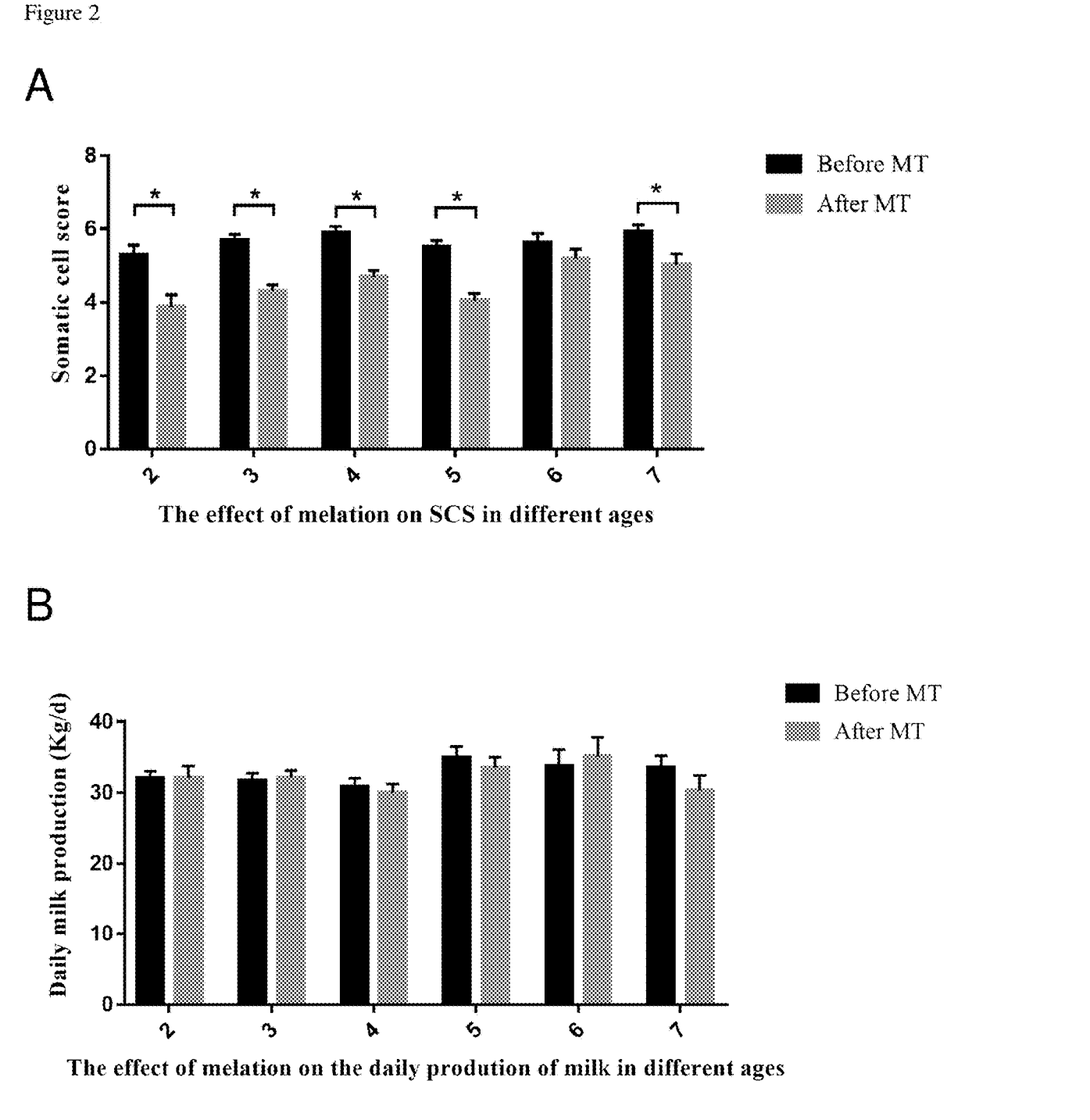
FIG. 2 is a diagram showing the effect of the injection of melatonin on DHI indicators of the milk from dairy cows of different ages.

The results are shown in FIG. 2, in which:
A. changes in somatic cell scores:
   2-year-old (5.30±0.27 VS 3.87±0.33),
   3-year-old (5.70±0.15 VS 4.31±0.18),
   4-year-old (5.89±0.17 VS 4.68±0.18),
   5-year-old (5.50±0.18 VS 4.04±0.19),
   6-year-old (5.63±0.26 VS 5.19±0.27), and
   7-year-old (5.91±0.20 VS 5.03±0.29);
B. changes in milk production:
   2-year-old (32.06±0.95 VS 32.12±1.63, kg/d),
   3-year-old (31.72±1.04 VS 32.11±0.96, kg/d),
   4-year-old (30.85±1.19 VS 30.03±1.22, kg/d),
   5-year-old (35.03±1.54 VS 33.56±1.52, kg/d),
   6-year-old (33.71±2.45 VS 35.19±2.67, kg/d), and
   7-year-old (33.54±1.73 VS 30.34±2.08, kg/d);
C. changes in protein contents:
   2-year-old (3.37%±0.07 VS 3.41%±0.09),
   3-year-old (3.43%±0.04 VS 3.44%±0.04),
   4-year-old (3.57%±0.06 VS 3.66%±0.06),
   5-year-old (3.44%±0.06 VS 3.55%±0.07),
   6-year-old (3.38%±0.07 VS 3.38%±0.07), and
   7-year-old (3.20%±0.06 VS 3.32%±0.07);
D. changes in lactose contents:
   2-year-old (5.20%±0.04 VS 5.19%±0.03),
   3-year-old (4.95%±0.03 VS 5.03%±0.02),
   4-year-old (4.80%±0.04 VS 4.94%±0.03),
   5-year-old (4.80%±0.04 VS 4.86%±0.05),
   6-year-old (4.85%±0.05 VS 4.91%±0.06), and
   7-year-old (4.90%±0.06 VS 4.93%±0.06);
E. changes in fat contents:
   2-year-old (4.65%±0.24 VS 4.54%±0.26),
   3-year-old (4.73%±0.12 VS 4.36%±0.11),
   4-year-old (4.97%±0.16 VS 4.69%±0.13),
   5-year-old (4.83%±0.14 VS 4.62%±0.16),
   6-year-old (5.14%±0.18 VS 5.27%±0.21), and
   7-year-old (5.16%±0.37 VS 4.66%±0.37);
F. changes in dry matter contents:
   2-year-old (13.91%±0.22 VS 13.87%±0.27),
   3-year-old (13.82%±0.12 VS 13.57%±0.13),
   4-year-old (14.19%±0.17 VS 14.18%±0.15),
   5-year-old (13.82%±0.17 VS 13.87%±0.18),
   6-year-old (14.14%±0.20 VS 14.13%±0.24), and
   7-year-old (13.80%±0.36 VS 13.48%±0.32);
G. changes in urea nitrogen contents:
   2-year-old (12.78±0.90 VS 13.90±0.80, mg/dL),
   3-year-old (14.09±0.53 VS 13.58±0.46, mg/dL),
   4-year-old (14.30±0.61 VS 13.32±0.49, mg/dL),
   5-year-old (14.95±0.52 VS 14.09±0.59, mg/dL),
   6-year-old (15.38±0.90 VS 15.79±0.94, mg/dL), and
   7-year-old (16.47±1.64 VS 15.11±1.34, mg/dL).

All data are expressed as mean±S.E.; the symbol "*" represents that there is significant differences between different groups; 2-year-old n=23; 3-year-old n=80; 4-year-old n=66; 5-year-old n=56; 6-year-old n=27; and 7-year-old n=19 (unit: number of cows).

(3) The somatic cell scores were significantly reduced by the injection of melatonin in different lactation stages, and were significantly reduced in mid-lactation (3.92±0.25 VS 2.00±0.17) and end-lactation (31.58±1.22 VS 31.25±1.29, kg/d) (p<0.05) (FIG. 3A). The lactose contents were increased by the injection of melatonin, and were significantly increased in peak-lactation (3.47%±0.06 VS 3.35%±0.06) and end-lactation (3.49%±0.04 VS 3.40%±0.04) (FIG. 3D).

Figure 3:
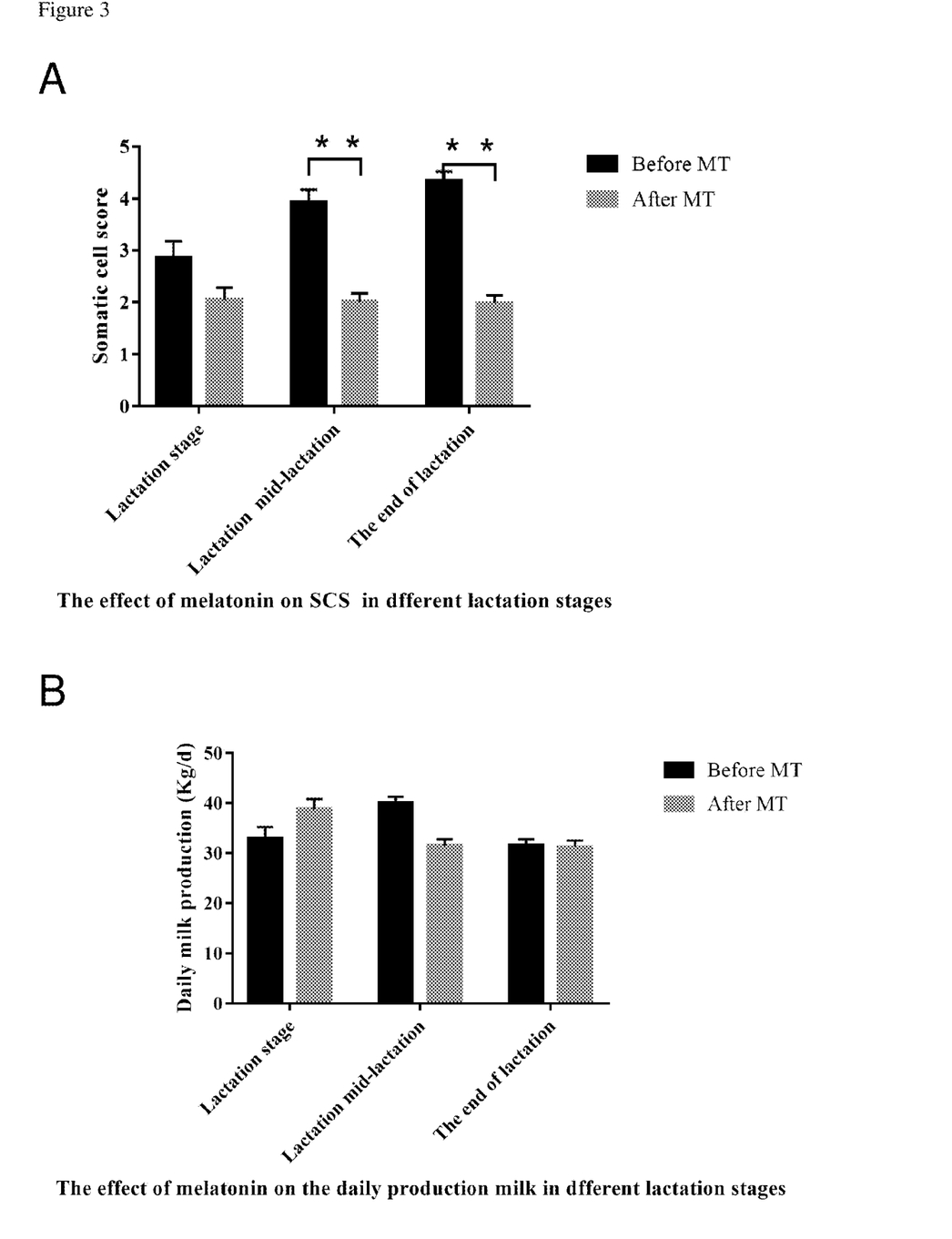
FIG. 3 is a diagram showing the effect of the injection of melatonin on DHI indicators of the milk from dairy cows of different lactation periods.

The results are shown in FIG. 3, in which:
A. changes in somatic cell scores:
peak-lactation (2.86±0.32 VS 2.04±0.24),
mid-lactation (3.92±0.25 VS 2.00±0.17), and
end-lactation (4.34±0.16 VS 1.99±0.15);
B. changes in milk production:
peak-lactation (32.93±2.34 VS 38.80±2.06, kg/d),
mid-lactation (39.98±1.35 VS 39.08±1.79, kg/d), and
end-lactation (31.58±1.22 VS 31.25±1.29, kg/d);
C. changes in protein contents:
peak-lactation (3.47%±0.06 VS 3.35%±0.06),
mid-lactation (3.45%±0.04 VS 3.45%±0.05), and
end-lactation (3.49%±0.04 VS 3.40%±0.04);
D. changes in lactose contents:
peak-lactation (5.15±0.05% VS 5.25%±0.04),
mid-lactation (5.14%±0.03 VS 5.19%±0.02), and
end-lactation (5.12%±0.03 VS 5.20%±0.02);
E. changes in fat contents:
peak-lactation (4.45%±0.19 VS 3.87%±0.26),
mid-lactation (4.20%±0.12 VS 4.22%±0.11), and
end-lactation (4.07%±0.08 VS 4.18%±0.12);
F. changes in dry matter contents:
peak-lactation (13.76%±0.16 VS 13.17%±0.29),
mid-lactation (13.49%±0.14 VS 13.56%±0.14), and
end-lactation (13.38%±0.09 VS 13.47%±0.13);
G. changes in urea nitrogen contents:
peak-lactation (11.93±0.65 VS 11.12±0.64, mg/dL),
mid-lactation (12.67±0.65 VS 12.11±0.54, mg/dL), and
end-lactation (11.45±0.38 VS 12.04±0.38, mg/dL);
wherein, peak-lactation n=15, mid-lactation n=38, end-lactation n=59 (unit: number of cows).

(4) The changes in the DHI indicators of Holstein cows were recorded for a whole year and were used to analyze the influence of melatonin on various DHI indicators. With the injection of melatonin, the somatic cell score was significantly (p<0.01) reduced by 63.54%, the fat content of milk was significantly (p<0.05) reduced by 11.31%, and the urea nitrogen content of milk was significantly (p<0.05) reduced by 11.08%. With the injection of melatonin, the protein content of milk was significantly (p<0.05) increased by 3.79%, and the lactose content was significantly (p<0.05) increased to 4.74%, and the daily milk production and dry matter content were also be influenced to a certain extent.

Figure 4:
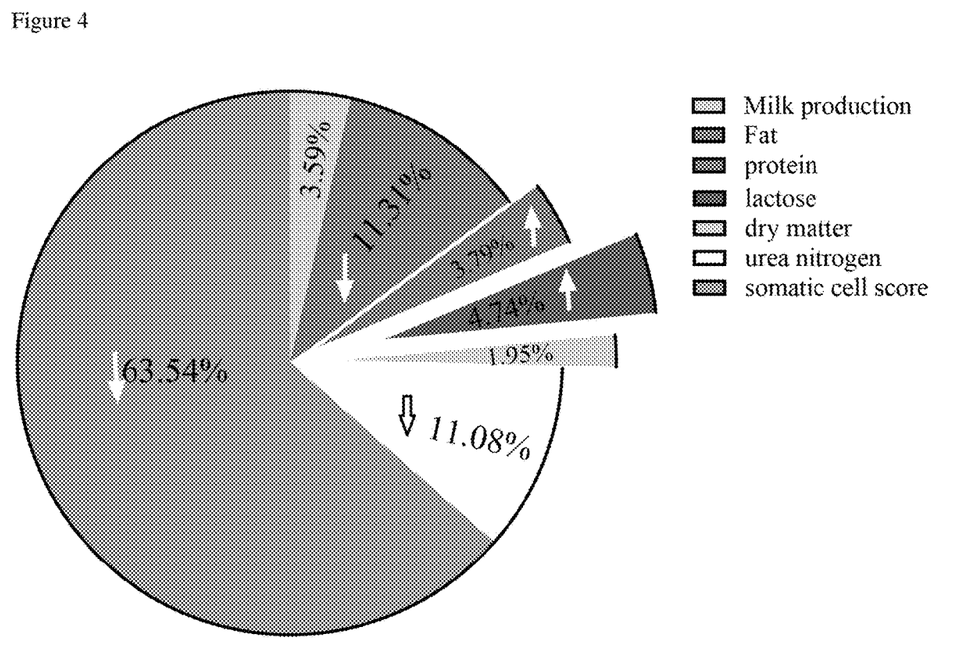
FIG. 4 is a diagram showing the analysis results of the effect of the injection of melatonin on DHI indicators.

The results are shown in FIG. 4.

As shown by FIG. 4, the DHI indicators including the somatic cell score, lactose content, urea nitrogen content, protein content and fat content were influenced significantly (p<0.05), in which the somatic cell score was most significantly affected (p<0.01), n=328 (unit: number of cows).

The present disclosure deeply analyzed the changes in the DHI indicators of milk after injecting exogenous melatonin, and reveals the mechanism in which melatonin improves the milk quality. The experimental results of the present disclosure demonstrate that the somatic cell counts in the milk of cows can be significantly reduced by injecting the dairy cows with 4.64 mg of melatonin for 4 consecutive days. It is also found that melatonin can reduce the concentration of cortisol, the number of white blood cells, lymphocytes and neutrophils; increase the concentrations of albumin, alanine aminotransferase and serum lactate dehydrogenase. The above research shows that the injection of melatonin can reduce the somatic cell counts in the milk of cows and increase the immunity of cows.

The present disclosure unexpectedly finds that it is simple to prepare an injection having melatonin as the main active ingredient, and the somatic cell counts in cow milk can be significantly reduced by injecting the melatonin injection into cows having somatic cell counts of 300,000/mL to 1,000,000/mL in different seasons, ages or lactation periods. This further shows that the melatonin injection according to the present disclosure can significantly reduce the somatic cell count in cow milk. At the same time, it is found by detecting the milk quality that the melatonin injection can not only increase the protein and dry matter contents in the milk, but also increase the lactose content in the milk, with reducing the fat and urea nitrogen contents in the milk. Thus, the melatonin injection of the present disclosure has more remarkable and excellent effects on improving milk quality.

The above examples are only used to describe the preferred embodiments of the present disclosure, but not intended to limit the scope of the present disclosure. Without departing from the spirit of the present disclosure, any variation and improvement made by those skilled person in the art based on the technical solutions of the present disclosure shall all fall within the protection scope defined by the attached claims of the present disclosure.

What is claimed is:

1. A composition for improving milk quality of a dairy cow, comprising melatonin as an active ingredient, absolute ethanol and physiological saline; wherein the concentration of melatonin in the composition is of 1 to 20 mg/mL, and the volume ratio of absolute ethanol to physiological saline is in a range of (1-3):(1-2).

2. The composition according to claim 1, wherein the volume ratio of absolute ethanol to physiological saline is 3:2.

3. A method for preparing the composition of claim 1, comprising the following steps: dissolving melatonin in absolute ethanol and then adding physiological saline, wherein the steps are carried out in dark, the concentration of melatonin in the composition is of 1 to 20 mg/ml, and the volume ratio of absolute ethanol to physiological saline is in a range of (1-3):(1-2).

4. The method according to claim 3, wherein the volume ratio of absolute ethanol to physiological saline is 3:2.

* * * * *